United States Patent [19]

Zuckerman

[11] 4,231,249
[45] Nov. 4, 1980

[54] APPARATUS AND METHODS FOR MONITORING CONCENTRATIONS OF TOXIC SUBSTANCES IN A WORK ENVIRONMENT

[75] Inventor: Matthew M. Zuckerman, Palo Alto, Calif.

[73] Assignee: Sierra Labs, Inc., Sunnyvale, Calif.

[21] Appl. No.: 22,285

[22] Filed: Mar. 20, 1979

[51] Int. Cl.³ .............................................. G01N 27/18
[52] U.S. Cl. ........................................ 73/23; 340/632
[58] Field of Search ................. 73/23, 27 R; 340/632, 340/633, 634, 636; 422/98; 23/232 E; 250/338, 340

[56] References Cited

U.S. PATENT DOCUMENTS

| 3,678,513 | 7/1972 | Ward, Jr. | 340/632 |
| 3,820,958 | 6/1974 | Cheng et al. | 422/98 |
| 3,925,666 | 12/1975 | Allan et al. | 340/632 |
| 4,166,380 | 9/1979 | Batz | 73/23 |

Primary Examiner—Stephen A. Kreitman
Attorney, Agent, or Firm—Donald C. Feix

[57] ABSTRACT

A portable, personal monitor measures and displays the concentrations of toxic substances to which an individual wearing the monitor has been exposed during a shift or other work period of the individual. The monitor is constructed in a compact, portable form, and it is enclosed within an outer case for wear by the individual during the work shift.

9 Claims, 1 Drawing Figure

APPARATUS AND METHODS FOR MONITORING CONCENTRATIONS OF TOXIC SUBSTANCES IN A WORK ENVIRONMENT

BACKGROUND OF THE INVENTION

This invention relates to apparatus and methods for measuring and displaying the concentrations of toxic substances in a working environment. It relates particularly to the monitoring, measuring, displaying and recording of concentration levels of such substances to which an individual worker is exposed as he moves around from place to place during a shift or other work period.

The Occupational Safety and Health Administration (OSHA) Act of 1970 emphasizes the need for standards to protect the health and to provide for the safety of workers exposed to potential hazards in their working environment.

The National Institute for Occupational Safety and Health (NIOSH) has conducted formal research to recommend standards for occupational exposure. The OSHA standards are currently established for approximately four hundred gases in a working environment. The standards are set in conformance to one or more of the following categories of concentration for each gas.

(a) Acceptable ceiling concentration (ACC). Under this standard an employee's exposure to a material shall not exceed at any time during an eight hour shift the acceptable ceiling concentration limit given for the material. If this level is not exceeded there is no chronic toxicity associated with the employee's exposure.

(b) An eight hour time-weighted average (TWA). Under this standard an employee's exposure to any material in an eight hour shift of a forty hour work week shall not exceed the eight hour time-weighted average limit given for that material.

(c) Ceiling value (CV). Under this standard an employee's exposure to any material shall at no time the ceiling value given for that material. Above this level the exposure becomes acutely toxic, and the employee is in danger of death or serious physical disability.

Some examples of these standards are:

| Material | ACC | TWA | CV |
| --- | --- | --- | --- |
| Methyl Chloride, ppm | 200 | 100 | 300 |
| Styrene, ppm | 200 | 100 | 600 |
| Hydrogen sulfide, ppm | 20 | 10 | 50 |
| Carbon Monoxide, ppm | — | 50 | — |
| Toluene, ppm | 300 | 200 | 500 |

To implement these standards it is necessary to have some equipment for monitoring the concentration levels to which the employee is exposed.

Fixed monitoring equipment has been used to sample the air in the working environment. The samples are analyzed for the concentration of the specific material. The fixed monitoring equipment has been equipped with monitoring devices that sound an evacuation alarm when the ceiling value (CV) is exceeded.

Other types of fixed monitoring equipment have continuously recorded the concentration data on strip charts. This information can be analyzed to determine if the working environment did exceed the OSHA standards at any time during the period the data was recorded.

A major problem with fixed monitoring equipment is that the sampling which occurs at various points in the working area is not necessarily directly related to the concentration to which an individual worker has been exposed in his breathing area.

To lessen this problem sampling is sometimes done at several points in the work area. However, at best, the fixed monitors cannot be keyed to the individual worker. Air currents and differences in density of materials and gases often result in the failure of the fixed monitors to accurately monitor individual worker's exposure to the materials. The problem of possibly inaccurate readings by a fixed monitor is also increased when the worker moves around the work area or leaves the work area for periods of time during the work day. This can result in inaccurate measurements, particularly when the time-weighted average (TWA) is calculated from the fixed monitor concentration output.

Portable monitors have been developed for wear by the workers. However, these monitors were mainly directed at warning the worker to evacuate the area by sounding an alarm if the material concentration exceeded an acceptable concentration for the material.

SUMMARY OF THE PRESENT INVENTION

It is an important object of the present invention to monitor the concentration of specific materials in the work environment for each individual worker.

A further object of the present invention is to read the concentration level periodically and to store the present concentration (PC), maximum concentration (MC), and the time-weighted average concentration (TWA) for the hours worked.

Another object is to compare the present concentration to the maximum concentration (of the concentration level previously experienced) and to store the present concentration as the new maximum concentration when the present concentration exceeds the previously experienced maximum concentration.

Another object is to compare the present concentration (PC) to a preset ceiling value (CV) and to sound an evacuation alarm if the present concentration equals or exceeds the ceiling value.

Another object is to compare the maximum concentration (MC) to a preset acceptable ceiling concentration (ACC) and to sound an alarm if the maximum concentration equals or exceeds the acceptable ceiling concentration.

Another object is to compare the calculated time-weighted average (TWA) to the OSHA TWA and to sound an alarm if the calculated time-weighted average equals or exceeds the OSHA time-weighted average.

Another object is to construct a monitor that at the end of a work shift is turned into an area foreman and from which the foreman can record for the specific worker the maximum concentration and the time-weighted average for that worker to check compliance with the OSHA standards.

Another object is to construct a portable monitor that can be connected to a fixed system by each worker and that will record the worker identification number or name, the shift time, date and the exposure in terms of the time-weighted average and maximum concentration and that will recharge the portable monitor in preparation for the next operating shift.

Another object is to construct an electronic system which is capable of operating with sensors specific to certain materials present in the work environment and of a size and configuration such that the electronic system can be housed in portable units in a limited space and powered by a battery and which will afford substantial resistance to damage by vibrations and shaking.

The monitor apparatus of the present invention includes a sensor, an analogue to digital signal convertor, a power supply, a microprocessor, a memory, a display and an alarm.

In a specific, preferred embodiment the monitor senses and measures concentration levels of hydrogen sulfide. The sensor in this embodiment of the present invention is a solid state type sensor which is covered by a porous metal cover. The surface of the sensing element is heated. When the hydrogen sulfide gas impinges on the surface of the sensing element, the resistance of the sensing element decreases in proportion to the concentration of the hydrogen sulfide gas.

Other embodiments of the monitor apparatus of the present invention include a tunable laser which operates at specific wave lengths in the infrared region to sense and to measure concentration levels by spectrophotometry. Approximately two hundred of the OSHA gases can be measured by infrared spectrophotometry.

Other embodiments of the present invention accomplish sensing by the use of chemically impregnated tapes that produce colorimetric responses to concentration levels of the toxic and/or hazardous materials. These changes in the impregnated tapes are then sensed by a photometer in the monitor instrument.

Apparatus and methods for monitoring concentrations of toxic or hazardous substances and which incorporate the structure and techniques described above and which are effective to function as described above constitue other, specific objects of this invention.

Other and further objects of the present invention will be apparent from the following description and claims and are illustrated in accompanying drawings which, by way of illustration, show preferred embodiments of the present invention and the principles thereof and what are now considered to be the best modes contemplated for applying these principles. Other embodiments of the invention embodying the same or equivalent principles may be used and structural changes may be made as desired by those skilled in the art without departing from the present invention and the purview of the appended claims.

BRIEF DESCRIPTIONS OF THE DRAWINGS

FIG. 1 is a block diagram of a monitor constructed in accordance with one embodiment of the present invention.

DESCRIPTION OF THE PREFERRED EMBODIMENTS

Figure 1:
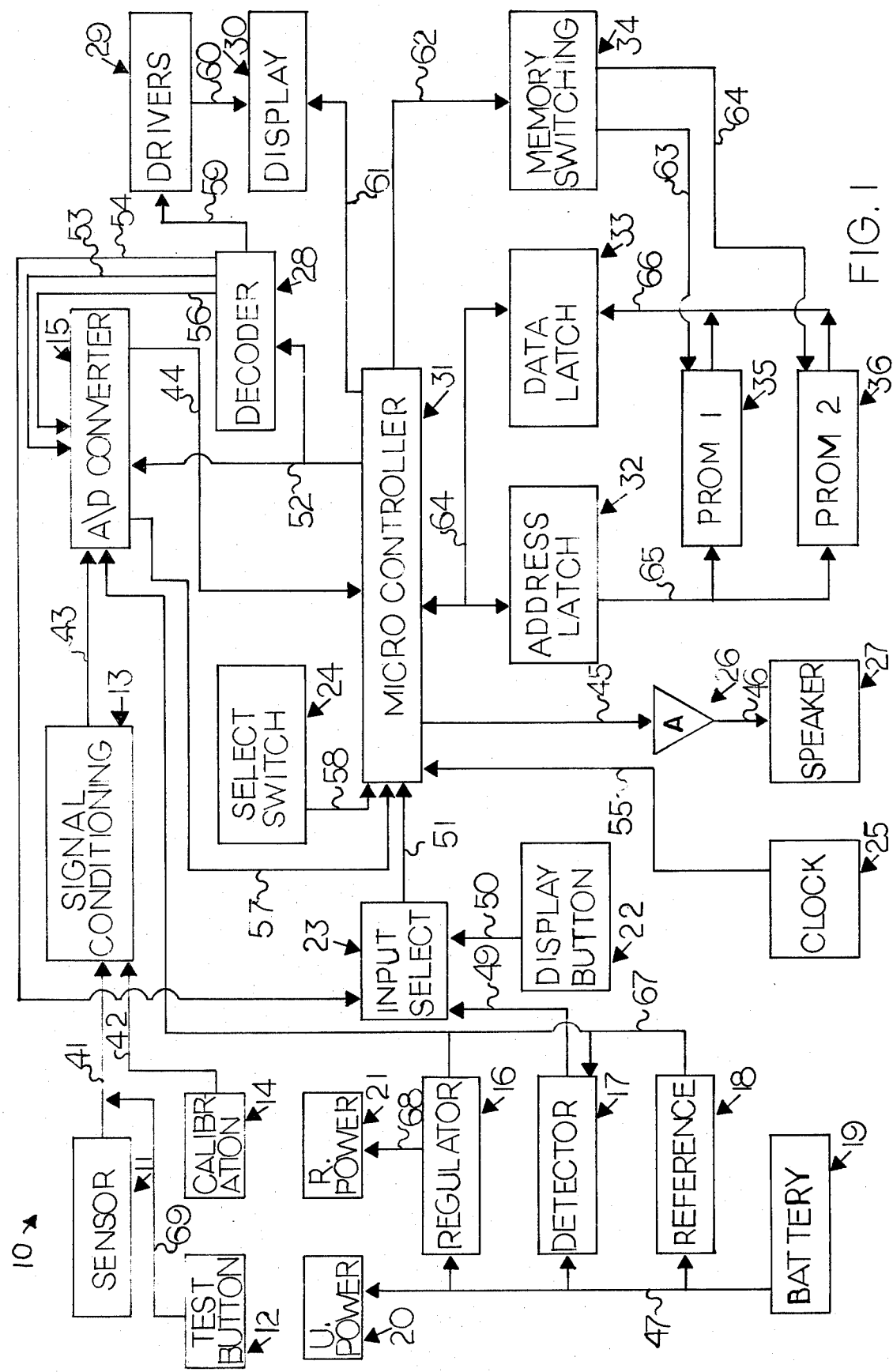

A monitoring system and apparatus for monitoring concentration levels of toxic and/or hazardous materials in a working environment and constructed in accordance with one embodiment of the present invention is indicated generally by the reference numeral 10 in FIG. 1.

In the specific embodiment shown in FIG. 1, the monitor 10 incorporates a sensor 11 which is of the solid state type and which responds to hydrogen sulfide gas in the range of zero to fifty parts per million (PPM) by producing a change in resistance. The signal is sent over the line 41 to a signal conditioning device 13 in which the analog resistance signal is converted into an analog voltage with the zero set and the span set by the input through a line 42 from a calibration device 14. In a specific embodiment the signal conditioning device 13 is an analog circuit with precision instrumentation operational amplifiers, resistors for zero and span adjustment and circuit components.

The signal then travels over the line 43 to an analog to digital convertor 15. In a specific embodiment a model number ADC 3511 convertor manufactured by National Semiconductor Corporation is used.

The signal is converted to a digital signal in the convertor 15 and is sent to a microcontroller 31 over a line 44. A model number 402N microcontroller manufactured by National Semiconductor Corporation Corporation is used in a specific embodiment of the monitor 10.

The microcontroller 31 performs a number of functions. It takes in the present concentration of the hydrogen sulfide gas, and it stores the value in one register. It calculates the time-weighted value of the gas concentration and stores that value in a register. It compares the present reading to the maximum concentration experienced since the monitor 10 was started at the beginning of a shift. And it stores the present reading as a new peak in the register if the present reading exceeds the previous maximum concentration. It stores the time that the unit has been turned on. The microcontroller 31 also compares the present concentration to an acceptable ceiling concentration. For this particular embodiment the acceptable ceiling concentration is 20 PPM. If the present concentration exceeds the acceptable ceiling concentration, the microcontroller sends a signal through a line 45 to an amplifier 26. The amplifier 26 in turn sends a signal over a line 46 to a speaker 27 and produces an audible sound indicating to the worker wearing the monitor that he should leave the work area.

Audible alarms (of different frequencies) are similarly produced when the time-weighted average concentration exceeds 10 PPM for the shift and when the present concentration exceeds 50 PPM (the ceiling value).

The audible alarm is also sounded when a detector 17 is fed a low voltage signal over a line 47 from a power supply battery. The low voltage signal indicates a low, unregulated voltage condition. The voltage reference 18, a voltage regulator 16 and certain other devices in the system are fed unregulated power from an unregulated power distribution system 20.

The alarm also sounds under the condition of a low reference voltage from the reference 18 over the line 48 to the convertor 15 and to the detector 17.

The status of the voltage is transmitted to the microcontroller 31 through an input select device 23 which takes information as to voltage status through a line 49 and request for display over a line 50 and multiplexes these two signals and feeds it into the microcontroller 31 over the line 51.

The control of the multiplexing comes from the microcontroller 31 over a line 52 which is connected to the decoder 28 and to the convertor 15.

The convertor 15 is disabled by a signal from the decoder 28 over the line 53 at the time the signal received by the decoder 28 over the line 52 is sent over the line 54 to the input select device 23. When the signal on the line 54 is high, the display request is fed into the microcontroller 31 over the line 51. When the signal on the line 54 is low, the battery status is fed into the microcontroller 31 over the line 51.

A clock 25 sends a signal over a line 55 to the microcontroller 31 to set the sequencing of all input and output calculation functions.

A further function of the clock timed signal is used by the microcontroller 31 to activate the amplifier 26 at various pulse rates so as to produce different frequencies of audible alarms from the speaker 27 for the various alarm conditions of acceptable ceiling concentration exceeded (chronic toxicity condition), time-weighted average concentration exceeded (chronic toxicity condition), ceiling value concentration (acute toxicity condition) exceeded and low voltage conditions.

The input of data in the digital form from the convertor 15 to the microcontroller 31 is controlled on a one binary coded decimal digit at a time basis where the digit is selected by a signal over the line 52 when the convertor 15 is not disabled by a low signal on a line 53 from the decoder 28.

The start of the conversion is a signal on the line 56 from the decoder 26 to the convertor 15. When the conversion is complete, a signal is sent from the convertor 15 to the microcontroller 31 over the line 57.

The quantity to be displayed as time the unit is on, the present concentration, the time-weighted average concentration, or the peak concentration experienced during the work shift is selected by positioning the select switch 24. The status of the select switch 24 is fed to the microcontroller 31 over the line 51.

When a request for a display of one of the four values is made by depressing the display button 22, each digit in the four digit display is sequentially selected to be turned on by a signal from the microcontroller 31 over the line 52 through the decoder 28 and over the line 59 to a driver in the drivers unit 29. In a specific embodiment the decoder is a model number CMOS 4555 dual two line to four line demultiplexer.

The seven segment data to illuminate the required segments is conveyed through a signal through a line 61 from the microcontroller 31.

The microcontroller 31 utilizes a programmable read only memory containing the control memory for the system. The memory comprises two program read only memories 35 and 36 (PROMs). In a specific embodiment the PROMs are Bipolar 3624 series with 512 by 8 bit words. The selection of memory 35 or memory 36 is controlled by a signal over a line 62 from the microcontroller 31 to a memory switching device 34 which in turn activates memory 35 by a signal over line 63 or memory 36 by a signal over a line 64.

The memory switching device 34 is also used in the system to conserve battery power by only activating when it is required by the microcontroller 31.

The line 64 is a bidirectional line through which address information and data are transmitted from the microcontroller 31 to an address latch 32 and a data latch 33.

When address information is sent through the line 64 to the address latch 32, the latch holds the address and sends it through a line 65 to either memory 35 or memory 36 whichever has been activated. The activated memory then sends the information stored at that address location over a line 66 to the data latch 33 which in turn sends the data over the line 64 to the microcontroller 31.

The reference voltage is transmitted to the voltage regulator 16 and to the convertor 15 over a line 67.

The regulated voltage is sent over a line 68 to the regulated power supply distribution system 21 to all the system components which require a regulated power supply.

The correct functioning of the system is electrically checked for the alarm condition of high hydrogen sulfide concentration requiring evacuation of personnel by depressing a test button 12 which simulates a high concentration of hydrogen sulfide being detected. The test button closure sends a resistive signal over the line 69 to a line 41 which transmits the signal to the signal conditioning device 13. The device 13 in turn sends a signal over a line 43 to the convertor 15 which enters the signal in the microcontroller 31 over the line 57.

The microcontroller 31 with the aid of the memory and other peripheral devices determines that the signal received is in excess of the maximum concentration of fifty parts per million and causes the high frequency signal to be sent over a line 45 to the amplifier 26 which in turn sends a signal over the line 46 to produce the audible evacuation alarm at the speaker 27.

The monitoring system is calibrated by exposing the sensor 11 to various known concentrations of hydrogen sulfide gas, placing the select switch 24 into the present concentration position, engaging the display button 22, and making an adjustment of the zero and span in the calibration device 14 so that the display indicates zero and some known concentration of hydrogen sulfide. The memory 35 and 36 have to be precalibrated with sensor response data so that only two points of calibration are required. One point being hydrogen sulfide free air (zero concentration), and the other point being a known concentration of hydrogen sulfide.

While a specific embodiment has been illustrated and described using a solid state sensor 11 for sensing and measuring concentration levels of hydrogen sulfide, other embodiments of the present invention use different sensors for sensing other materials.

A tunable laser is used in some embodiments of the present invention to operate at specific wave lengths in the infrared region, and approximately two hundred of the OSHA gases can be measured by the infrared spectrophotometry using the tunable laser sensor.

Other embodiments of the present invention use chemically impregnated tapes for producing colorimetric responses to concentration levels. These changes in the tape are then sensed by a photometer in the monitor 10.

While I have illustrated and described the preferred embodiments of my invention, it is to be understood that these are capable of variation and modification, and I therefore do not wish to be limited to precise details set forth but desire to avail myself to such changes and alterations as fall into the purview of the following claims.

I claim:

1. A portable, personal monitor for measuring and displaying the concentrations of toxic substances to which an individual wearing the monitor is exposed during a shift or other work period of the individual, said monitor comprising, sensor means for sensing the concentration level of the toxic substance in the air ambient to the monitor and effective to produce an analog signal having a magnitude dependent on the concentration level, convertor means for converting the analog signal to a digital signal corresponding to the sensed concentration level, controller means for
(a) indicating the present concentration level sensed by the monitor, (b) determining and storing the maximum concentration level sensed during the work period, and
(c) computing and storing a time-weighted average of the concentration levels sensed during the work period, and case means for mounting and housing the sensor means, convertor means, and controller means and constructed for wear by an individual whose exposure to the toxic substance is to be monitored during the work period.

2. The invention defined in claim 1 including a program read only memory precalibrated with the response of the sensor means so that only two points of calibration of the sensor means are required, one point being a zero concentration level of the substance and the other calibration point being a known concentration level of the substance.

3. The invention defined in claim 1 including alarm means operatively associated with the controller means for sounding audible alarms to indicate the worker is exposed to concentration levels which have been determined by regulatory agencies to constitute acute or chronic toxicity exposure when any of the following conditions occur:
(a) an acceptable ceiling concentration level is exceeded, above which level chronic toxicity condition exists,
(b) a ceiling value concentration level is exceeded, above which acute toxicity condition exits, and
(c) a time-weighted average concentration level is exceeded, above which a chronic toxicity condition exists.

4. The invention defined in claim 1 including display means for presenting a numerical display of the sensed concentration level.

5. The invention defined in claim 4 including input selector means for selectively causing the display means to display any of
(a) the maximum concentration level sensed during the work period,
(b) the present concentration level sensed by the monitor, and
(c) the time-weighted average of the concentration levels sensed during the work period.

6. The invention defined in claim 1 including readout means for transferring the duration of the work period, the stored maximum concentration level and the stored time-weighted average of the concentration level sensed during the work period to another recording apparatus at the end of the shift or other work period.

7. A method of monitoring a working environment to measure and display the concentrations of toxic substances to which an individual has been exposed during a shift or other work period of the individual, said method comprising,
attaching a portable, personal monitor to the individual for wear by the individual continuously throughout the shift or other work period,
sensing the concentration level of a toxic substance in the air ambient to the monitor,
producing an analog signal having a magnitude dependent on the sensed concentration level,
converting the analog signal to a digital signal corresponding to the sensed concentration level,
indicating in the monitor the present concentration level being sensed,
determining and storing in the monitor the maximum concentration level sensed during the work period, and
computing and storing in the monitor a time-weighted average of the concentration level sensed during the work period.

8. The method defined in claim 7 including transferring from the monitor the duration of the work period, the stored maximum concentration level, and the stored time-weighted average of the concentration level sensed during the work period to another recording means at the end of the shift or other work period.

9. The method defined in claim 7 including a sounding an audible alarm to indicate the worker is exposed to concentration levels which have been determined by regulatory agencies to constitute acute or chronic toxicity exposure when any of the following conditions occur:
(a) an acceptable ceiling concentration level is exceeded, above which level chronic toxicity condition exists,
(b) a ceiling value concentration level is exceeded, above which acute toxicity condition exists, and
(c) a time-weighted average concentration level is exceeded, above which a chronic toxicity condition exists.

* * * * *